US011214782B2

(12) United States Patent
Chen et al.

(10) Patent No.: US 11,214,782 B2
(45) Date of Patent: Jan. 4, 2022

(54) METHOD OF TREATING GLYCOGEN STORAGE DISEASE TYPE VI

(71) Applicant: Duke University, Durham, NC (US)

(72) Inventors: Yuan-Tsong Chen, Durham, NC (US); Priya Kishnani, Durham, NC (US); Baodong Sun, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 16/843,436

(22) Filed: Apr. 8, 2020

(65) Prior Publication Data

US 2020/0299663 A1 Sep. 24, 2020

Related U.S. Application Data

(62) Division of application No. 15/659,549, filed on Jul. 25, 2017, now Pat. No. 10,647,969, which is a division of application No. 14/701,470, filed on Apr. 30, 2015, now Pat. No. 9,850,474, which is a division of application No. 12/737,394, filed as application No. PCT/US2009/003993 on Jul. 8, 2009, now Pat. No. 9,050,333.

(60) Provisional application No. 61/129,612, filed on Jul. 8, 2008.

(51) Int. Cl.
    *C12N 9/26* (2006.01)
    *A61K 38/47* (2006.01)
(52) U.S. Cl.
    CPC ............ *C12N 9/2408* (2013.01); *A61K 38/47* (2013.01); *C12Y 302/0102* (2013.01)
(58) Field of Classification Search
    CPC ..................................................... A61K 38/47
    USPC .................................................... 424/94.63
    See application file for complete search history.

(56) References Cited

U.S. PATENT DOCUMENTS

| 7,056,712 B2 | 6/2006 | Chen |
| 2002/0110551 A1 | 8/2002 | Chen |

FOREIGN PATENT DOCUMENTS

| WO | WO 00/34451 | 6/2000 |

OTHER PUBLICATIONS

Kilimann et al., Glycogen pathways in disease: new developments in a classical field of medical genetics. J Inherit Metab Dis (2015) 38:483-487.*
Product Monograph for Myozyme (alglucosidase alfa—recombinant human acid alpha glucosidase)—Revision dated Dec. 16, 2016—54 pages—published by Sanofi Genzyme—available at https://products.sanofi.ca/en/myozyme-en.pdf.

Suppl. European Search Report dated Jan. 31, 2012 issued in connection with EP Appln. No. 09 79 4820.
Tsao et al., "A Hypotonic Infant With Complete Deficiencies of Acid Maltase and Debrancher Enzyme." J. Child Neural., 9:90-91 (1994).
Van Diggelen et al., "Debranching enzyme in Fibroblasts, amniotic fluid cells and chorionic villi: pre- and postnatal diagnosis of glycogenosis type III." Clinica Chimica Acta, 149:129-134 (1985).
Wu et al., "Expression of Catalytically Active Human Multifunctional Glycogen-Debranching Enzyme and Lysosomal Acid Alpha-Glucosidase in Insect Cells." Biochemistry and Molecular Biology International, 39(4):755-764 (1996).
Yi et al., "Characterization of a canine model of glycogen storage disease type llla." Disease Models & Mechanisms, 5:804-811 (2012).
Kilimann et al, "Glycogen pathways in disease: new developments in a classical field of medical genetics." J Inherit Metab Dis, 38(3):483-487 (2015).
Bates et al., "Debranching enzyme from rabbit skeletal muscle; evidence for the location of two active centres on a single polypeptide chain." FEBS Lett. 58(1):181-85 (Oct. 1975).
Braun et al., "Identification of Asp 549 as the catalytic nucleophile of glycogen-debranching enzyme via trapping of the glycosyl-enzyme intermediate." Biochemistry 35(17):5458-5463 (Apr. 1996).
Brown, "Diagnosis of glycogen storage disease," In: Congenital Metabolic Diseases Diagnosis and Treatment, Wapnir RA, (ed)., Dekker, New York, pp. 227-250 (1985).
Chen and Burchell, "Glycogen storage diseases." In: The Metabolic and Molecular Bases of Inherited Disease, C R. Scriver et al, eds., 7th Edition McGraw-Hill/New York, pp. 935-965 (1995).
Coleman et al., "Glycogen storage disease type III (glycogen debranching enzyme deficiency): correlation of biochemical defects with myopathy and cardiomyopathy." Annals of Internal Medicine 116(11):896-900 (Jun. 1992).
Cornelio et al., "Clinical varieties of neuromuscular disease in debrancher deficiency." Arch. Neurol. 41(10):1027-1032 (Oct. 1984).
Dimauro et al., "Glycogen metabolism of human diploid fibroblast cells in culture. I. Studies of cells from patients with glycogenosis types II, III, and V." Pedatr. Res. 7(9):739-744 (Sep. 1973).
Fuller et al., "Isolation and characterisation of a recombinant, precursor form of lysosomal acid alpha-glucosidase." Eur. J Biochem. 234(3):903-909 (Dec. 1995).
Gillard and Nelson, "Amylo-1,6-glucosidase/4-alpha-glucanotransferase: use of reversible substrate model inhibitors to study the binding and active sites of rabbit muscle debranching enzyme." Biochemistry 16(18):3978-3987 (Sep. 1977).
Gregory et al., "Glycogen storage disease type llla in curly-coated retrievers." J. Vet. Intern. Med. 21(1):40-46 (Jan.-Feb. 2007).
Soliman et al., "Cardiac Involvement in Adults with Pompe Disease", J. Intern. Med., 264(4):333-339 (2008).
Hirschhorn, Glycogen Storage Disease Type II: Acid .alpha.-glucosidase (Acid Maltase) Deficiency. In: The Metabolic and Molecular Bases of Inherited Disease, C. R. Scriver et al, eds., 7th Edition McGraw-Hill/New York, pp. 2443-2464 (1995).

(Continued)

*Primary Examiner* — Sheridan Swope
(74) *Attorney, Agent, or Firm* — Polsinelli PC; Michelle L. McMullen

(57) ABSTRACT

The disclosure relates, in general, to Glycogen Storage Disease Type VI and, in particular, to a method of treating Glycogen Storage Disease Type VI and to compounds and compositions suitable for use in such a method.

14 Claims, 5 Drawing Sheets

Specification includes a Sequence Listing.

(56) References Cited

OTHER PUBLICATIONS

Jespersen et al., "Starch- and glycogen-debranching and branching enzymes: prediction of structural features of the catalytic (beta/alpha)8-barrel domain and evolutionary relationship to other amylolytic enzymes." Journal of Protein Chemistry 12(6):791-805 (Dec. 1993).
Chen et al. Chapter 71; Glycogen Storage Diseases, in the Online Metabolic & Molecular Bases of Inherited Disease, Valle D et al. Editors (2008) (48 pages).
Konigsberg, "Skeletal myoblasts in culture." Methods in Enzymology 58:511-527 (1979).
Liu et al., "Molecular cloning, sequencing, and analysis of the cDNA for rabbit muscle glycogen debranching enzyme." Arch Biochem Biophys 306(1):232-239 (Oct. 1993).
Liu et al., "Effects of oligosaccharide binding on glycogen debranching enzyme activity and conformation." Biochemistry 34(21):7056-7061 (May 1995).
Markowitz et al., "A man with type III glycogenosis associated with cirrhosis and portal hypertension." Gastroenterology 105(6):1882-1885 (Dec. 1993).
Mendelsohn et al., "Elimination of antibodies to recombinant enzyme in Pompe's disease." N. Engl. J. Med. 360(2):194-195 (Jan. 2009).
Miranda et al., "Glycogen debrancher deficiency is reproduced in muscle culture." Ann. Neural. 9(3):283-288 (Mar. 1981).
Mumtaz et al., "Design of liposomes for circumventing the reticuloendothelial cells." Glycobiology 1(5):505-510 (Nov. 1991).
Nilsson et al., "Induction of immune tolerance in patients with hemophilia and antibodies to factor VIII by combined treatment with intravenous IgG, cyclophosphamide, and factor VIII." N. Engl. J. Med. 318(15):947-950 (Apr. 1988).
Onodera et al., "Substrate specificity and subsite affinities of rabbit liver acid alpha-glucosidase." J. Biochem. 116(1):7-11 (Jul. 1994).
Talente et al., "Glycogen storage disease in adults." Annals. Intern. Med. 120(3):218-226 (Feb. 1994).
Van der Ploeg et al., "Breakdown of lysosomal glycogen in cultured fibroblasts from glycogenosis type II patients after uptake of acid alpha-glucosidase." J Neurol. Sci. 79(3):327-336 (Jul. 1987).
Van Hove et al., "High-level production of recombinant human lysosomal acid alpha-glucosidase in Chinese hamster ovary cells which targets to heart muscle and corrects glycogen accumulation in fibroblasts from patients with Pompe disease." Proc. Natl. Acad. Sci. 93(1):65-70 (Jan. 1996).
Webster et al., "Isolation of human myoblasts with the fluorescence-activated cell sorter." Experimental Cell Research 174(1):252-265 (Jan. 1988).
Yang et al., "Definitive prenatal diagnosis for type III glycogen storage disease." Am. J. Hum. Genet. 47(4):735-739 (Oct. 1990).
Yang et al., "Molecular basis of the enzymatic variability in Type III glycogen storage disease (GSD-III)." Am. J. Hum. Genet. 51(Suppl): Abstract 102, p. A28 (Oct. 1992).
Yang et al., "Molecular cloning and nucleotide sequence of cDNA encoding human muscle glycogen debranching enzyme." J. Biol. Chem. 267(13):9294-9299 (May 1992).
Yang-Feng et al, "Assignment of the human glycogen debrancher gene to chromosome 1p21." Genomics 13(4):931-934 (Aug. 1992).
Moses et al., "The Variable Presentations of Glycogen Storage Disease Type IV: A Review of Clinical, Enzymatic and Molecular Studies." Current Molecular Medicine 2(2):177-188 (Mar. 2002).
Yi et al., "Alglucosidase alfa treatment alleviates liver disease in a mouse model of glycogen storage disease type IV." Molecular Genetics and Metabolism Reports 9:31-33 (2016).
Human acid 1-gluosidase from www.drugbank.ca/drugs/DB01272. Downloaded Mar. 26, 2017.
Ozen, "Glycogen storage diseases: New perspectives." World J. Gastroenterol 13(18):2541-2553 (May 2007).
Arad et al., "Glycogen Storage Diseases Presenting as Hypertrophic Cardiomyopathy." N Engl J Med., 352(4):362-372 (2005).
Auricchio et al., "Purification of an acid alpha-glucosidase by dextran-gel filtration." Biochem J, 5(1):35-8 (1967).
Askanas et al., "Adult-Onset Acid Maltase Deficiency—Morphologic and Biochemical Abnormalities Reproduced in Cultured Muscle " N Engl J Med., 294:573-578 (1976).
Bao et al., "Isolation and nucleotide sequence of human liver glycogen debranching enzyme mRNA: identification of multiple tissue-specific isoforms." Gene, 197(1-2):389-98 (1997).
DeDuve et al., "Functions of lysosomes." Annu Rev Physiol, 28:435-492 (1966).
Dunn, "Studies on the Mechanisms of Autophagy: Maturation of the Autophagic Vacuole." The Journal of Cell Biology, 110:1935-1945 (1990).
International Search Report for PCT/US2009/003993, dated Mar. 8, 2010.
Iwamasa et al., "Glycogen Storage Disease, Studies Related to the Mechanism of Glycogenosome Formation." Path. Res. Pract., 176:236-252 (1983).
Joseph et al., "Immune Tolerance Induction to Enzyme-Replacement Therapy by Co-Administration of Short-Term, Low-Dose Methotrexate in a Murine Pompe Disease Model." Clin Exp Immunol., 152(1):138-146 (2008).
Kundu et al., "Autophagy: Basic Principles and Relevance to Disease." Ann. Rev. Pathol. Mech. Dis., 3:427-55 (2008).
Lee et al., "A biochemical and pharmacological comparison of enzyme replacement therapies for the glycolipid storage disorder Fabry disease." Glycobiology, 13(4):305-13 (2003).
Martiniuk et al., "Corection of Glycogen Storage Disease Type II by Enzyme Replacement with a Recombinant Human Acid Maltase Produced by Over-Expression in a CHO-DHFRneg Cell Line." Biochemical and Biophysical Research Communications, 276(3):917-923 (2000).
McVie-Wylie et al., "Biochemical and Pharmacological Characterization of Different Recombinant Acid Alpha-Glucosidase Preparations Evaluated for the Treatment of Pompe Disease." Mol Genet Metab, 94(4):448-455 (2008).
Shen et al., "Mutations in Exon 3 of the Glycogen Debranching Enzyme Gene Are Associated with Glycogen Storage Disease Type III That Is Differentially Expressed in Liver and Muscle." J. Clin. Invest., 98(2):352-357 (1996).

* cited by examiner

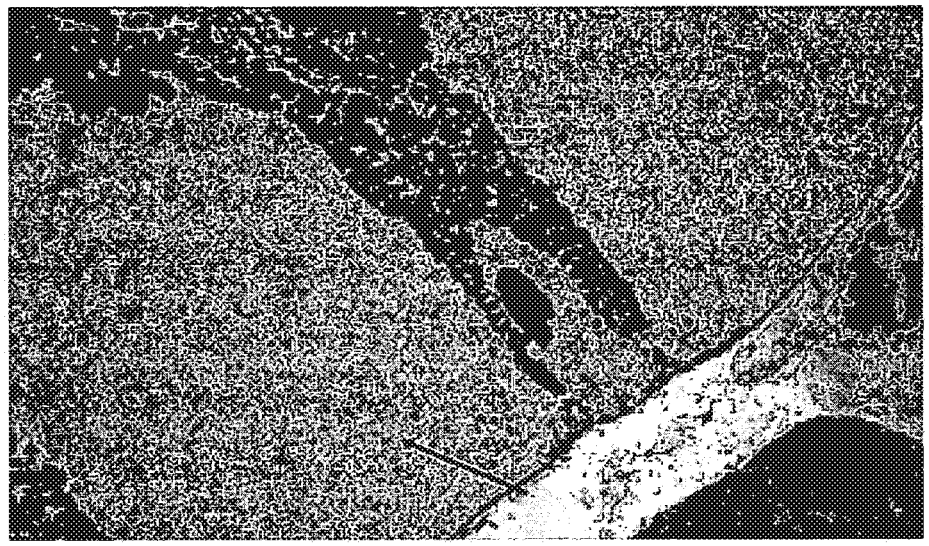
Figure 2. cytoplasmic glycogen forming lakes within myocyte under EM (patient MG)
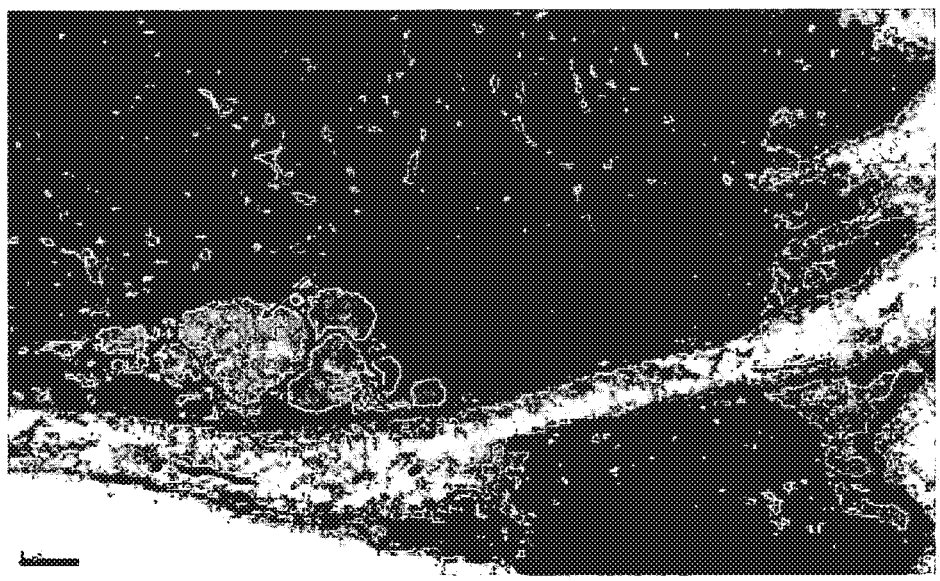
Figure 3. Lysosomal glycogen was seen within myocyte (patient MG)

SEQUENCE LISTING

```
<160> NUMBER OF SEQ ID NOS: 1

<210> SEQ ID NO 1
<211> LENGTH: 952
<212> TYPE: PRT
<213> ORGANISM: homo sapiens

<400> SEQUENCE: 1

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro Arg Val His Ser Arg Ala Pro Ser Pro Leu
        195                 200                 205

Tyr Ser Val Glu Phe Ser Glu Glu Pro Phe Gly Val Ile Val His Arg
    210                 215                 220
```

-continued

```
Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
        355                 360                 365

Leu Gly Phe His Leu Cys Arg Trp Gly Tyr Ser Ser Thr Ala Ile Thr
370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
        435                 440                 445

Ser Gly Pro Ala Gly Ser Tyr Arg Pro Tyr Asp Glu Gly Leu Arg Arg
450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
            500                 505                 510

Asp Gly Met Trp Ile Asp Met Asn Glu Pro Ser Asn Phe Ile Arg Gly
        515                 520                 525

Ser Glu Asp Gly Cys Pro Asn Asn Glu Leu Glu Asn Pro Pro Tyr Val
530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
        595                 600                 605

Tyr Ala Gly His Trp Thr Gly Asp Val Trp Ser Ser Trp Glu Gln Leu
610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
```

-continued

```
                    645                 650                 655
Leu Cys Val Arg Trp Thr Gln Leu Gly Ala Phe Tyr Pro Phe Met Arg
            660                 665                 670

Asn His Asn Ser Leu Leu Ser Leu Pro Gln Glu Pro Tyr Ser Phe Ser
            675                 680                 685

Glu Pro Ala Gln Gln Ala Met Arg Lys Ala Leu Thr Leu Arg Tyr Ala
    690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
                740                 745                 750

Thr Pro Val Leu Gln Ala Gly Lys Ala Glu Val Thr Gly Tyr Phe Pro
                755                 760                 765

Leu Gly Thr Trp Tyr Asp Leu Gln Thr Val Pro Ile Glu Ala Leu Gly
    770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
                835                 840                 845

Lys Gly Gly Glu Ala Arg Gly Glu Leu Phe Trp Asp Asp Gly Glu Ser
    850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
            885                 890                 895

Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
    915                 920                 925

Ser Pro Asp Thr Lys Val Leu Asp Ile Cys Val Ser Leu Leu Met Gly
    930                 935                 940

Glu Gln Phe Leu Val Ser Trp Cys
945                 950
```

METHOD OF TREATING GLYCOGEN STORAGE DISEASE TYPE VI

CROSS-REFERENCE TO RELATED APPLICATIONS

This application is a divisional of U.S. application Ser. No. 15/659,549, filed on Jul. 25, 2017, which is now U.S. Pat. No. 10,647,969, which is a divisional of U.S. application Ser. No. 14/701,470, filed on Apr. 30, 2015, which is now U.S. Pat. No. 9,850,474, which is a divisional of U.S. application Ser. No. 12/737,394, filed on Jan. 7, 2011, which is now U.S. Pat. No. 9,050,333, which is the U.S. national phase of International Application No. PCT/US2009/003993, filed on Jul. 8, 2009, which designated the U.S. and claims the benefit of priority from U.S. Provisional Application No. 61/129,612, filed on Jul. 8, 2008, the entire contents of each of which are incorporated herein by reference.

REFERENCE TO THE SEQUENCE LISTING

The Sequence Listing submitted 24 Jun. 2021 as a text file named "15_667_US_DIV3_Sequence_Listing_ST25", created on 24 Jun. 2021 and having a size of 9 kilobytes, is hereby incorporated by reference pursuant to 37 C.F.R. § 1.52(e)(5).

TECHNICAL FIELD

The present invention relates, in general, to Glycogen Storage Disease and, in particular, to a method of treating Glycogen Storage Disease-type-III and to compounds and compositions suitable for use in such a method.

BACKGROUND

Glycogen debranching enzyme (GDE) is a multifunctional enzyme acting as 1,4-α-D-glucan: 1,4-α-D-glucan 4-α-D-glycosyltransferase (E.C 2.4.1.25) and amylo-1,6-glucosidase (E.C 3.2.1.33) in glycogen degradation. The two activities of the debranching enzyme are believed to reside at separate sites on a single polypeptide chain with a molecular mass of 174 kDa. The structure-function domain has not been studied in detail (Chen and Burchell, Glycogen storage disease. In: The Metabolic and Molecular Bases of Inherited Disease, C. R. Scriver et al, eds., 7$^{th}$ Edition McGraw-Hill/New York, pp. 935-965 (1995); Bates et al, FEBS Lett. 58:181-185 (1975); Gillard et al, Biochemistry 16:3978-3987 (1977); Chapter 71 Kishnani P S; Koeberl D, Chen Y T. Glycogen Storage Diseases, in The Online Metabolic & Molecular Bases of Inherited Disease, Valle D, Beaudet A L, Vogelstein B, Kinzler K W, Antonarakis S E, Ballabio A, Scriver C R, Sly W S, Childs B, Editors (2008)). The predominant form of cDNA that encodes human debrancher has a 4596 bp coding region and a 2371 bp 3' nontranslated region (Yang et al, J. Biol. Chem. 267:9294-9299 (1992)). Tissue specific debrancher mRNAs exist. These isoforms differ at the 5' nontranslated region and are believed to be generated by differential RNA transcription and splicing from a single debrancher gene (Bao et al, Gene 197:389-398 (1997)). The human gene is localized to chromosome 1p21 (Yang-Feng et al, Genomics 13:931-934 (1992)). The genomic structure of the human GDE gene has been determined and consists of 35 exons spanning ~85 kb of DNA.

Debranching enzyme, together with phosphorylase, is responsible for complete degradation of glycogen. Liver and muscle are the two major organs most active in glycogen metabolism. The primary function of glycogen in these organs is different. In muscle, glycogen provides a local fuel store for short-term energy consumption. In liver, it maintains glucose homeostasis.

Genetic deficiency of glycogen debranching enzyme (Glycogen Storage Disease-type III, GSD-III) causes an incomplete glycogenolysis resulting in accumulation of glycogen with abnormally short outer chain in various organs. The commonly affected organs in GSD-III are liver, skeletal muscle and heart. The disease is characterized by hepatomegaly, hypoglycemia, short stature, variable myopathy and cardiomyopathy. Patients with this disease vary remarkably, both clinically and enzymatically (Markowitz et al, Gastroenterology 105:1882-1885 (1993); Shen et al, J. Clin. Invest. 98:352-357 (1996); Telente et al, Annals. Intern. Med. 120:218-226 (1994)). Most patients have disease involving both liver and muscle (type IIIa), some patients (~15% of all GSD-III patients) have only liver involvement (type IIIb), and, in rare cases, there is a selective loss of only one of the two GDE activities (glucosidase, (type IIIc) or transferase (type IIId)). Liver symptoms in GSD-III can improve with age and may disappear after puberty. Overt liver cirrhosis has been seen in some patients, some have developed hepatocellular carcinoma. Muscle weakness, though minimal during childhood, may become predominant in adults with onset in the third or fourth decade. These patients have slowly progressive proximal weakness and distal muscle wasting and some patients become wheelchair bound. Even within the subgroup of patients who develop myopathy/cardiomyopathy there is clinical variability. Some patients have asymptomatic cardiomyopathy, some have early symptomatic cardiomyopathy leading to death, and some have only muscle and no apparent heart involvement. An abnormal electrocardiogram (ECG) with ventricular hypertrophy is a frequent finding and does not correlate with clinical severity. Normal serum creatine kinase levels do not rule out muscle enzyme deficiency. The biochemical subtypes do not predict clinical severity.

There appears to be no correlation between the amount of debrancher protein and clinical severity (Yang et al, Am. J. Hum. Genet. 41:A28 (1992)). To predict accurately at initial diagnosis whether myopathy or cardiomyopathy may occur, one must determine whether debranching enzyme activity is deficient in muscle (Chen and Burchell, Glycogen storage disease. In: The Metabolic and Molecular Bases of Inherited Disease, C. R. Scriver et al, eds., 7$^{th}$ Edition McGraw-Hill/New York, pp. 935-965 (1995)). It appears that muscle disease will not develop in patients with GDE activity retained in muscle (Coleman et al, Annals of Internal Medicine 116:896-900 (1992)).

The variable phenotype is, in part, explained by differences in tissue-specific expression of the defective enzyme. As pointed out above, in type IIIa, enzyme is deficient in both liver and muscle, in IIIb there is enzyme deficiency only in liver. Unlike phosphorylase, which has tissue-specific isoenzymes encoded by different genes, at the protein level and at the molecular level it appears that there are no tissue-specific GDE isoenzymes in different tissues. Until now, it has not been understood in GSD-III how a single GDE gene, normally expressed in all tissues, can change expression in different tissues (Chen and Burchell, Glycogen storage disease, In: The Metabolic and Molecular Bases of Inherited Disease, C. R. Scriver et al, eds., 7$^{th}$ Edition McGraw-Hill/New York, pp. 935-965 (1995)). Two mutations (17delAG and G6X), both located in exon 3 at amino acid codon 6, are exclusively found in the GSD-IIIb (Shen et al, J. Clin. Invest. 98:352-357 (1996)) suggesting that exon 3 is important in controlling tissue-specific expression of the GDE gene.

Histology of the liver in these patients is characterized by a universal distension of hepatocytes by glycogen and the presence of fibrous septa. Electron microscopy studies on muscle specimens have shown presence of accumulated glycogen beneath the sarcolemma and between myofibrils; the excess glycogen not only disperses in the cytoplasm, but is also seen in the lysosomes (Cornelio et al, Arch. Neurol. 41:1027-1032 (1984), Miranda et al, Ann. Neurol. 9:283-288 (1981)).

The detailed structural biology of GDE is not known, although several functional domains of glycogen debranching enzyme have been proposed from enzymological studies and sequence comparison to other enzymes with similar catalytic function (Yang et al, J. Biol. Chem. 267:929409299 (1992), Liu et al, Archives of Biochemistry and Biophysics 306:232-239 (1993), Liu et al, Biochemistry 34:7056-7061 (1995), Jespersen et al, Journal of Protein Chemistry 12 (6):791-805 (1993)). A region at the COOH-terminal of the debranching enzyme could be a candidate for glycogen binding site (Yang et al, J. Biol. Chem. 267:9294-9299 (1992)), and 4 regions at N-terminal half of the enzyme bear sequence homology to the catalytic sites identified or proposed in other amylolytic enzymes (Liu et al, Archives of Biochemistry and Biophysics 306:232-239 (1993), Jespersen et al, Journal of Protein Chemistry 12 (6):791-805 (1993)). Aspartate at position 549 has been identified as the catalytic nucleophile in the transferase site of rabbit muscle glycogen debranching enzyme (Braun et al, Biochemistry 35:5458-5463 (1996)).

Currently there is no effective treatment for the disease. Hypoglycemia can be controlled by frequent meals high in carbohydrates with cornstarch supplements or nocturnal gastric drip feedings. Patients with myopathy have been given diets high in protein during the daytime plus overnight enteral infusion. In some patients, transient improvement in symptoms has been documented but there are no long-term data demonstrating that the high protein diet prevents or treats the progressive myopathy (Chen and Burchell, Glycogen storage disease. In: The Metabolic and Molecular Bases of Inherited Disease, C. R. Scriver et al, eds., $7^{th}$ Edition McGraw-Hill/New York, pp. 935-965 (1995)). The progressive myopathy and/or cardiomyopathy is a major cause of morbidity in adults and patients with progressive liver cirrhosis and hepatic carcinoma have been reported. While gene therapy delivery of a normal, functional gene into the diseased organ could ultimately cure the disease, an ideal gene delivery vehicle that is reliable is currently not available. There is no living animal model for this disease. Dogs affected with GSD-III have been reported (Gregory et al, J. Vet. Intern. Med. 21 (1):40-46 (2007)), and a breeding colony is currently being established.

Enzyme replacement therapy has been effective in diseases in which the responsible enzymes/proteins exert their functions in extracellular fluids, such as adenosine deaminase deficiency, hemophilia, and $\alpha$1-antitrypsin deficiency, or in a lysosomal location such as a lysosomal storage disease. Enzyme replacement has not been explored in diseases in which the defective enzyme is present in cytosol (such as the debranching enzyme in GSD-III), presumably due to the lack of an efficient and specific cellular uptake mechanism that delivers exogenous enzyme across the plasma membrane into the cytoplasm. Liposomes can fuse with plasma membrane and deliver their content, however, the use of liposomes is compromised by lack of organ-specific tropism and clearance by the reticulo-endothelial system (Mumtaz et al, Glycobiology 1 (5):505-510 (1991)). For an effective treatment for GSD-III, the enzyme should be able to target muscle and heart as well as liver.

Cytoplasmic glycogen is normally digested by phosphorylase and debranching enzyme; excess glycogen taken up by lysosomes through autophagy can be digested by lysosomal acid $\alpha$-glucosidase (GAA). Deficiency of debranching enzyme activity results in massive accumulation of glycogen having abnormally short outer branches. The excess glycogen in GSD-III resides not only in the cytoplasm but also in the lysosomes (cytoplasm>lysosome) (Cornelio et al, Arch. Neurol. 41:1027-1032 (1984), Miranda et al, Ann. Neurol. 9:283-288 (1981)). This suggests that the "normal" GAA activity in GSD-III may not be sufficient to digest all the excess glycogen. GAA is a lysosomal exo 1,4-$\alpha$-D-glucosidase that hydrolyzes both $\alpha$-1,4 and $\alpha$-1,6 linkages of glycogen and can completely digest glycogen with and without abnormally short outer branches (Onodera et al, J. Biochem. 116:7-11 (1994)). GAA thus acts on glycogen with abnormally short outer branches such as accumulates in GSD-III. As this glycogen in GSD-III accumulates both in cytoplasm and lysosomes, providing more GAA may help to digest lysosomal glycogen and hence also cytoplasmic glycogen. It is postulated that, as the lysosomes are cleared of glycogen, glycogen from the cytoplasm shuffles into them thus decreasing the total amount of accumulated glycogen in GSD-III patients.

Deficiency of GAA causes Pompe disease (type II glycogen storage disease), a fatal metabolic myopathy with accumulation of glycogen in lysosome and cytoplasm (lysosome>cytoplasm) (Hirschhorn, Glycogen Storage Disease Type II: Acid $\alpha$-glucosidase (Acid Maltase) Deficiency. In: The Metabolic and Molecular Bases of Inherited Disease, C. R. Scriver et al, eds., $7^{th}$ Edition McGraw-Hill/New York, pp. 2443-2464 (1995)). Enzyme replacement therapy with mannose-6-Phosphate (man-6-P)-rich precursor recombinant human GAA results in efficient man-6-P receptor mediated endocytosis of the enzyme followed by reduction of both lysosomal and cytoplasmic glycogen in fibroblasts (Van Hove et al, Proc. Natl. Acad. Sci. 93:65-70 (1996)). In vivo, this enzyme targets heart and muscle as well as liver and spleen following intravenous injection in animals and in human Pompe patients. The rapid clearance of glycogen in Pompe fibroblasts when cultured in glucose-free medium suggests a ready mobilization of glycogen from both lysosomal and cytoplasmic compartments (Van Hove et al, Proc. Natl. Acad. Sci. 93:65-70 (1996), DiMauro et al, Pedatr. Res. 7:739-744 (1973)). It is contemplated that cytoplasmic glycogen continuously shuffles through lysosomes by autophagy for degradation.

The present invention results, at least in part, from the realization that administered GAA can reduce lysosomal glycogen in GSD-III patients and ultimately also reduce cytoplasmic glycogen. Some of the administered GAA may also go directly into the cytosol and reduce the glycogen. The invention provides a method of treating GSD-III (as well as GSD-IV, -VI, -IX, XI and cardiac glycogenosis due to AMP-activated protein kinase gamma subunit 2 deficiency) based on the use of GAA.

SUMMARY OF THE INVENTION

The present invention relates generally to GSD. More specifically, the invention relates to methods of treating GSD-III and to compounds and compositions suitable for use in such methods.

BRIEF DESCRIPTION OF THE DRAWINGS

FIG. 2. Cytoplasmic glycogen forming lakes within myocyte under EM in a patient with GSD-III.

FIG. 3. Lysosomal glycogen was seen within myocyte of a patient with GSD-III.

DETAILED DESCRIPTION OF THE INVENTION

Figure 1:
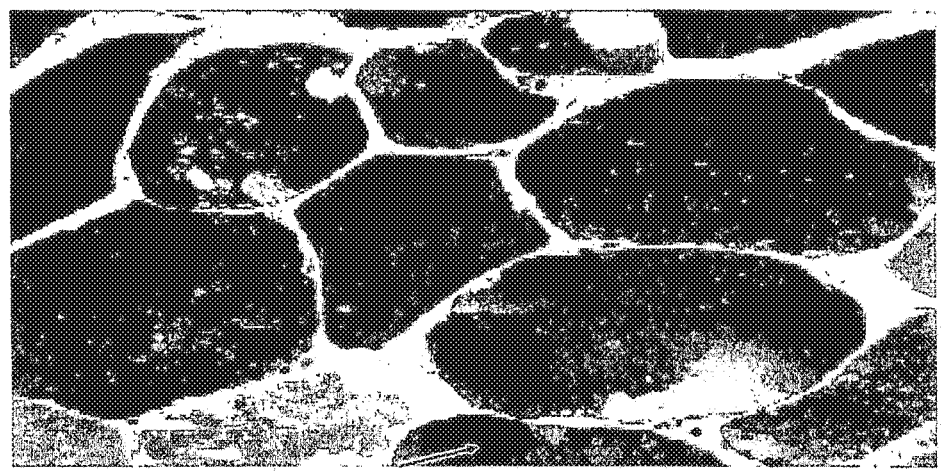
FIG. 1. The light microscopic appearance of the skeletal muscle biopsy from a GSD-IIIa patient. The glycogen is present as cytoplasmic lakes within myocytes. The glycogen is not membrane bound within lysosomes but is free flowing within the cytoplasm.

The present invention relates to a method of treating GSD, particularly GSD-III, by administering GAA to an individual suffering from the disease. The invention also relates to the use of the enzyme, GAA, in the manufacture of a medicament for the treatment of GSD (e.g., GSD-III). As described herein, patients suffering from, for example, GSD-III can be treated by administering GAA on, for example, a regular basis. Patients thus treated can be expected to demonstrate improvement of hypoglycemia, hepatomegaly, hepatic function, cardiac status, and/or muscular strength, as well as a reduction of tissue glycogen levels.

The invention makes possible the treatment of GSD-III, including GSD-type IIIa, type IIIb, type IIIc or type IIId. The invention also makes possible the treatment of other forms of GSD, including, but not limited to, GSD-IV, -VI, -IX, XI and cardiac glycogenosis due to AMP-activated protein kinase gamma subunit 2 deficiency.

The terms, "treat" and "treatment," as used herein, refer to amelioration of one or more symptoms associated with the disease, prevention or delay of the onset of one or more symptoms of the disease, and/or lessening of the severity or frequency of one or more symptoms of the disease. For example, treatment can refer to improvement of hypoglycemia, growth retardation, hepatomegaly, and hepatic function (e.g., reduction of SGOT, SGPT); cardiac status (e.g., reduction, amelioration or prevention of the progressive cardiomyopathy, arrhythmia and other cardiac manifestations that can be found, for example, in GSD-III), myopathy (e.g., exercise tolerance), reduction of glycogen levels in tissue (e.g, liver and muscle) of the individual affected by the disease, or any combination of these effects. Further, the treatment may prevent long term complications such as liver cirrhosis, hepatocellular carcinoma due to clearance of glycogen with an abnormal structure. In one preferred embodiment, treatment includes improvement of liver symptoms, particularly, in reduction or prevention of GSD (e.g., GSD-III)-associated hypoglycemia, hepatomegaly and abnormal liver function. The terms, "improve," "prevent" or "reduce," as used herein, indicate values that are relative to a baseline measurement, such as a measurement in the same individual prior to initiation of the treatment described herein, or a measurement in a control individual (or multiple control individuals) in the absence of the treatment described herein. A control individual is an individual afflicted with the same form of the disease (e.g., GSD-III) as the individual being treated, who is about the same age as the individual being treated (to ensure that the stages of the disease in the treated individual and the control individual(s) are comparable).

The individual being treated can be an individual (infant, child, adolescent, or adult human) having GSD-III. The individual can have residual GDE activity, or no measurable activity. In another preferred embodiment, the individual is an individual who has been recently diagnosed with the disease. Early treatment (treatment commencing as soon as possible after diagnosis) is important to minimize the effects of the disease and to maximize the benefits of treatment.

While the invention is described in detail with reference to GSD-III, the methods described herein can also be used to treat individuals suffering from other GSDs, including, but not limited to, GSD-IV, -VI, IX and -XI. The methods described herein can also be used in the treatment of individuals suffering from cardiac glycogenosis due to AMP-activated protein kinase gamma subunit 2 deficiency.

In the methods of the invention, GAA (preferably, human GAA) is administered to the individual. The GAA is in a form that, when administered, targets tissues such as the tissues affected by the disease (e.g., liver, heart or muscle). In one preferred embodiment, human GAA is administered in its precursor form, as the precursor contains motifs that allow efficient receptor-mediated uptake of GAA. Alternatively, a mature form of human GAA that has been modified to contain motifs to allow efficient uptake of GAA into cells, can be administered. In a particularly preferred embodiment, the GAA is the precursor form of recombinant human GAA.

GAA is obtainable from a variety of sources. In a particularly preferred embodiment, recombinant human acid α-glucosidase (rhGAA) produced in Chinese hamster ovary (CHO) cell cultures is used (see, e.g., Fuller, M. et al., Eur. J. Biochem. 234:903 909 (1995); Van Hove, J. L. K. et al., Proc. Natl. Acad. Sci. USA 93:65 70 (1996) and U.S. Pat. No. 7,056,712). Production of GAA in CHO cells yields a product having glycosylation that allows significant and efficient uptake of GAA in tissues such as heart and muscle. MYOZYME (alglucosidase alpha) Genzyme Corp.), or other recombinant human GAA, can be used in accordance with the invention.

The GAA has a specific enzyme activity in the range of about 1.0-8.0 µmol/min/mg protein, preferably in the range of about 4.0-8.0 µmol/min/mg protein. In one preferred embodiment, the GAA has a specific enzyme activity of at least about 1.0 µmol/min/mg protein; more preferably, a specific enzyme activity of at least about 4.0 µmol/min/mg protein; even more preferably, a specific enzyme activity of at least about 6.0 μmol/min/mg protein; and still more preferably, a specific enzyme activity of at least about 8.0 μmol/min/mg protein.

GAA can be administered alone, or in compositions or medicaments comprising the GAA, as described herein. The compositions can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. In a preferred embodiment, a water-soluble carrier suitable for intravenous administration is used.

The composition or medicament, if desired, can also contain minor amounts of wetting or emulsifying agents, or pH buffering agents. The composition can be a liquid solution, suspension, emulsion, tablet, pill, capsule, sustained release formulation, or powder. The composition can also be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

The composition or medicament can be formulated in accordance with the routine procedures as a pharmaceutical composition adapted for administration to human beings. For example, in a preferred embodiment, a composition for intravenous administration typically is a solution in sterile isotonic aqueous buffer. Where necessary, the composition can also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

The GAA can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

GAA (or composition or medicament containing GAA) is administered by an appropriate route. In one embodiment, the GAA is administered intravenously. In other embodiments, GAA is administered by direct administration to a target tissue, such as heart or muscle (e.g., intramuscular). In yet another embodiment, GAA is administered orally. More than one route can be used concurrently, if desired.

GAA (or composition or medicament containing GAA) can be administered alone, or in conjunction with other agents, such as antihistamines (e.g., diphenhydramine) or immunosuppressants or other immunotherapeutic agents which counteract anti-GAA antibodies. Possible immunomodulation strategies include preventive tolerance induction either with initiation of therapy, or tolerance modulation after the development of inhibitory antibodies. The term, "in conjunction with," indicates that the agent is administered at about the same time as the GAA (or composition containing GAA). For example, the agent can be mixed into a composition containing GAA, and thereby administered contemporaneously with the GAA; alternatively, the agent can be administered contemporaneously, without mixing (e.g., by "piggybacking" delivery of the agent on the intravenous line by which the GAA is also administered, or vice versa). In another example, the agent can be administered separately (e.g., not admixed) but within a short time frame (e.g., within 24 hours) of administration of the GAA. In one embodiment, GAA (or composition containing GAA) is administered in conjunction with an immunosuppressive or immunotherapeutic regimen designed to reduce amounts of, or prevent production of, anti-GAA antibodies. For example, a protocol similar to those used in hemophilia patients (Nilsson, I. M. et al., N. Engl. J. Med. 318:947 50 (1988)) can be used to reduce anti-GAA antibodies. In a particularly preferred embodiment, the immunosuppressive or immunotherapeutic regimen is begun prior to the first administration of GAA, in order to minimize the possibility of production of anti-GAA antibodies. As an example, use of Rituximab, which eliminates mature B cells expressing CD20, methotrexate, which acts on both B and T cells, or different combinations of such agents is possible (Mendehlson et al, N. Engl. J. Med. 360 (2):194-195 (2009)).

GAA (or composition or medicament containing GAA) is administered in a therapeutically effective amount (i.e., a dosage amount that, when administered, for example, at regular intervals, is sufficient to treat the disease, such as by ameliorating symptoms associated with the disease, preventing or delaying the onset of the disease, and/or also lessening the severity or frequency of symptoms of the disease, as described above). The amount that will be therapeutically effective in the treatment the disease will depend on the nature and extent of the disease's effects, and can be determined by standard clinical techniques. In addition, in vitro or in vivo assays can optionally be employed to help identify optimal dosage ranges. The precise dose to be employed can also depend on the route of administration, and the seriousness of the disease, and should be decided according to the judgment of a practitioner and each patient's circumstances. Effective doses can be extrapolated from dose-response curves derived from in vitro or animal model test systems. In a preferred embodiment, the therapeutically effective amount is less than about 40 mg enzyme/kg body weight of the individual, preferably in the range of about 1-40 mg enzyme/kg body weight, and even more preferably about 20 mg enzyme/kg body weight or about 10 mg enzyme/kg body weight. The effective dose for a particular individual can be varied (e.g., increased or decreased) over time, depending on the needs of the individual. For example, in times of physical illness or stress, or if anti-GAA antibodies become present or increase, or if disease symptoms worsen, the amount can be increased.

The therapeutically effective amount of GAA (or composition or medicament containing GAA) can be administered at regular intervals, depending on the nature and extent of the disease's effects, and on an ongoing basis. Administration at a "regular interval," as used herein, indicates that the therapeutically effective amount is administered periodically (as distinguished from a one-time dose). The interval can be determined by standard clinical techniques. In preferred embodiments, GAA is administered monthly, bimonthly, weekly, twice weekly, or daily. The administration interval for a single individual need not be a fixed interval but can be varied over time, depending on the needs of the individual. For example, in times of physical illness or stress, if anti-GAA antibodies become present or increase, or if disease symptoms worsen, the interval between doses can be decreased.

In one preferred embodiment, a therapeutically effective amount of 20 mg enzyme/kg body weight is administered bi-monthly. In another preferred embodiment, a therapeutically effective amount of 10 mg enzyme/kg body weight is administered weekly or 5 mg enzyme/kg body weight is administered twice weekly.

The invention additionally pertains to a pharmaceutical composition comprising human GAA, as described herein, in a container (e.g., a vial, bottle, bag for intravenous administration, syringe, etc.) with a label containing instructions for administration of the composition for treatment of GSD-III, such as by the methods described herein.

Certain aspects of the invention are described in greater detail in the non-limiting Examples that follow. (See also U.S. Pat. No. 7,056,712.)

Example 1

GAA is a lysosomal exo 1,4-α-D-glucosidase that hydrolyzes both α-1,4 and, α-1,6 linkage of glycogen. A highly efficient system has been developed for producing human GAA which targets heart and muscle and corrects glycogen accumulation in patients with Pompe disease. The excess glycogen in GSD-III resides not only in the cytoplasm but also in the lysosome (Cornelio et al, Arch. Neurol. 41:1027-1032 (1984), Miranda et al, Ann. Neurol. 9:283-288 (1981)). This suggests that excess cytoplasmic glycogen is shuffled more effectively into the lysosomes than can be cleared by the "normal" GAA activity in GSD-III cells. It is hypothesized that cytoplasmic glycogen continuously shuffles through lysosomes by autophagy for degradation, and that the administered GAA can reduce lysosomal glycogen in GSD-III and ultimately also reduce cytoplasmic glycogen.

Source of the Enzyme

High GAA producing CHO cells can be grown in expanded culture and recombinant enzyme purified from the medium. Milligram quantities of purified GAA is available weekly as part of an ongoing project on the development of enzyme replacement therapy for Pompe disease. MYOZYME (Genzyme Corp.), or other rhGAA (preferably CHO-produced), is suitable for use in the instant invention.

Tissue Source

Muscle samples can be obtained from patients with GSD-IIIa whose disease has been previously diagnosed by demonstrating debrancher activity deficiency in both liver and muscle. Needle muscle biopsy from patients with the diagnosis can be performed. It is expected that at least 3 patients with a confirmed diagnosis of GSD-IIIa will be studied. The needle muscle biopsy can obtain 50-70 mg of tissues sufficient for analysis. The procedure is less invasive than an open biopsy. Currently, skin fibroblasts from 9 GSD-IIIa patients are available. An IRB approved protocol is available that makes it possible to obtain muscle and skin tissue from patients with GSD III.

Cell Culture

Cultured skin fibroblasts and muscle cells can be used to test the feasibility of using GAA to treat GSD-III. The focus will be particularly on IIIa patients who have, in addition to hepatomegaly, progressive myopathy (increasing muscle weakness by muscle strength testing in 6 months to 1 year follow-up and/or clinical complaints of a decrease in muscle strength) and cardiomyopathy (increase in left ventricular mass in a 6-12 month period on follow-up), and also patients with progressive liver disease. Deficiency of debranching enzyme and accumulation of glycogen are present in skin fibroblasts and muscle cells grown in culture from GSD-III patients (Miranda et al, Ann. Neurol. 9:283-288 (1981), DiMauro et al, Pedatr. Res. 7:739-744 (1973), Yang et al, Am. J. Hum. Genet. 47:735-739 (1990), Brown, Diagnosis of glycogen storage disease, In: Wapnir P A, (ed)., Congenital Metabolic Disease Diagnosis and Treatment, Dekker, New York, pp. 227-250 (1985)). Cultured muscle cells also reflect muscle biopsy findings in that both cytoplasmic and lysosomal glycogen are observed (Cornelio et al, Arch. Neurol. 41:1027-1032 (1984), Miranda et al, Ann. Neurol. 9:283-288 (1981)). The skin fibroblasts and muscle cultures can, therefore, be used to improve understanding of the pathogenesis of the disease and to evaluate approaches to therapy. Muscle cultures can be established from muscle biopsy samples using a protocol similar to the isolation of quail myoblasts (Konigsberg, Methods in Enzymology 45:511-527 (1979)). Replating of the primary cultures can be performed to select against fibroblasts. If the biopsy sample is too small, a more efficient myoblasts isolation method using the fluorescence-activated cell sorter can be performed (Webster, Experimental Cell Research 174:252-265 (1988)). Myoblasts can be allowed to differentiate to myotubes by changing the medium to 2% horse serum. Muscle cells in the appropriate stage will be used for conduct of the experiments.

Effect on Glycogen with GAA Treatment

Glycogen concentrations in skin fibroblasts vary with cell confluence and passage number (DiMauro et al, Pedatr. Res. 7:739-744 (1973)). Experiments can be performed at near confluence, and each patient can serve as his/her own control by concurrent duplicate testing with and without GAA treatment. Dose response (from 500 to 5000 nmol/hr/ml of GAA) and time course (1 to 10 days) can be tested for the effect of glycogen reduction. Glycogen content can be measured in total cell homogenates and also individually in cytosol and crude lysosomal fractions (van der Ploeg et al, J. Neurol. Sci. 79:327-336 (1987)). Electromicroscopic examination can be performed for evidence of clearance in both cytoplasm and lysosomes.

To avoid obscuring of the results by the continuous glycogen synthesis that occurs in cells cultured in the presence of glucose in the medium, cells can be shifted to glucose-free medium 24 hours after GAA treatment. Deprivation of glucose resulted in greater than 80% drop of glycogen in the normal cells, but only 30% reduction in GSD-III cells (Yang et al, Am. J. Hum. Genet. 47:735-739 (1990), Brown, Diagnosis of glycogen storage disease, In: Wapnir P A, (ed)., Congenital Metabolic Disease Diagnosis and Treatment, Dekker, New York, pp. 227-250 (1985)). Thus sufficiently high levels of glycogen persist which allow accurate evaluation of GAA treatment. The persistent glycogen in GSD-III cells have short outer brancher which can be assessed using glucose-1-phosphate formed from endogenous polysaccharide by phosphorylase (Yang et al, Am. J. Hum. Genet. 47:735-739 (1990)).

Example 2 below includes a description of studies that have been undertaken.

Example 2

Primary human skeletal muscle cultures from GSD-IIIa patients have been established as an in vitro model to evaluate efficacy of rhGAA for treatment of GSD-III. Myoblasts were isolated from three GSD-IIIa patients and one healthy volunteer. Histopathology of these muscle biopsies was examined by light and electronic microscopy (EM) to confirm abnormal glycogen accumulation in these GSD-IIIa patients. The light microscopic appearance of the skeletal muscle biopsies from GSD-IIIa patients showed abundant glycogen accumulation in cytoplasmic pools (FIG. 1). Under EM, the vast majority of the glycogen was found free in the cytoplasm along with small amount of membrane-bound glycogen (FIGS. 2 and 3).

Figures 4A, 4B:
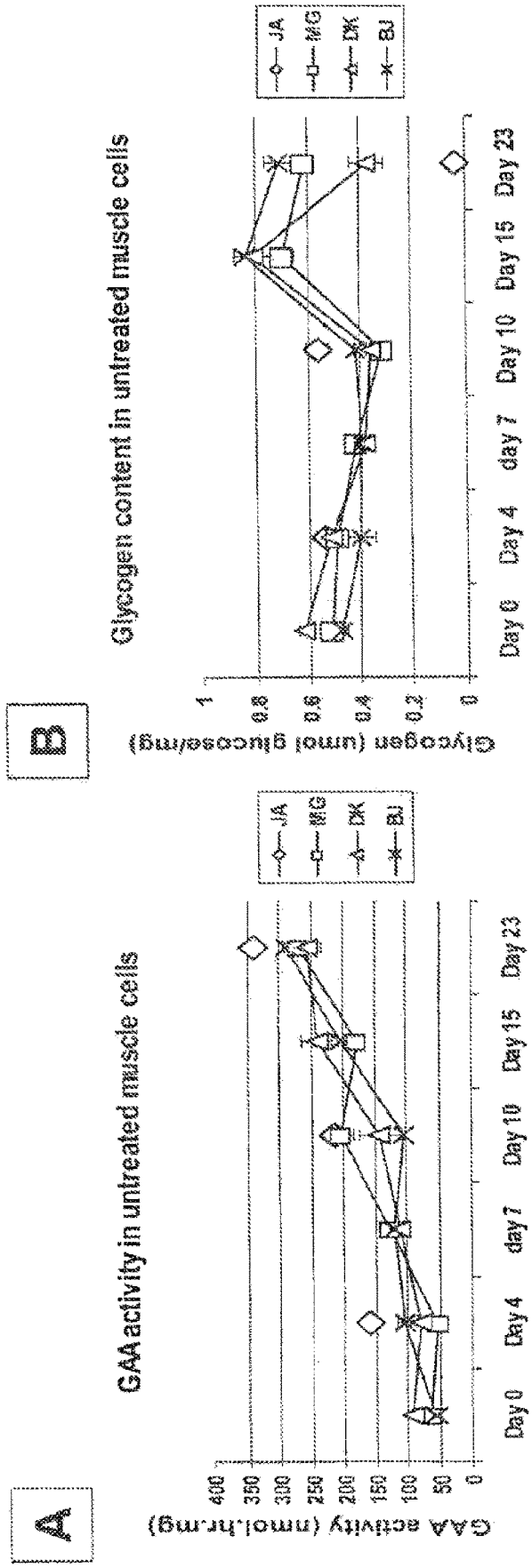
FIGS. 4A and 4B. Pattern of glycogen accumulation in muscle cells derived from a normal subject and 3 GSD-III patients. Duplicate cultures were harvested at times indicated. Cellular GAA activity (FIG. 4A) and glycogen content (FIG. 4B) were determined in duplicates for each culture (mean±SD).
Figures 5A, 5B:
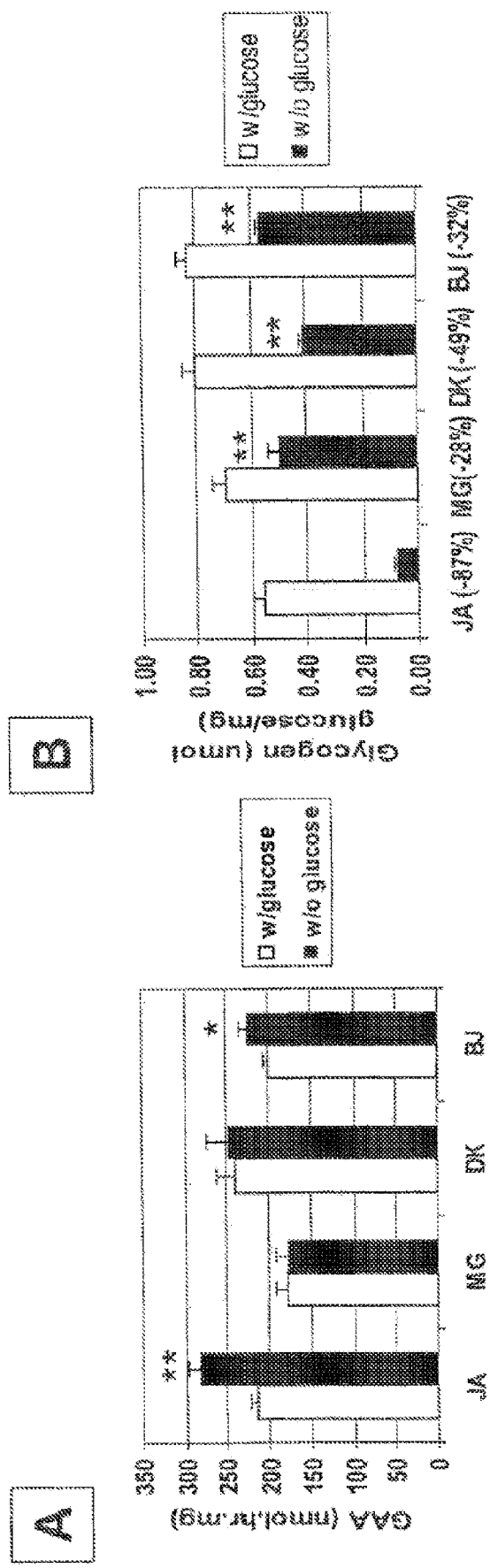
FIGS. 5A and 5B. Glycogen depletion in untreated muscle cells by glucose starvation. GAA activity (FIG. 5A) and glycogen content (FIG. 5B) were analyzed in GSD-III muscle cells after 48-hour culturing (from Day 13 to Day 15) in differentiation medium with (w/) glucose or without (w/o) glucose. (*, p value<0.01; **, p<0.001).
Figure 6A:
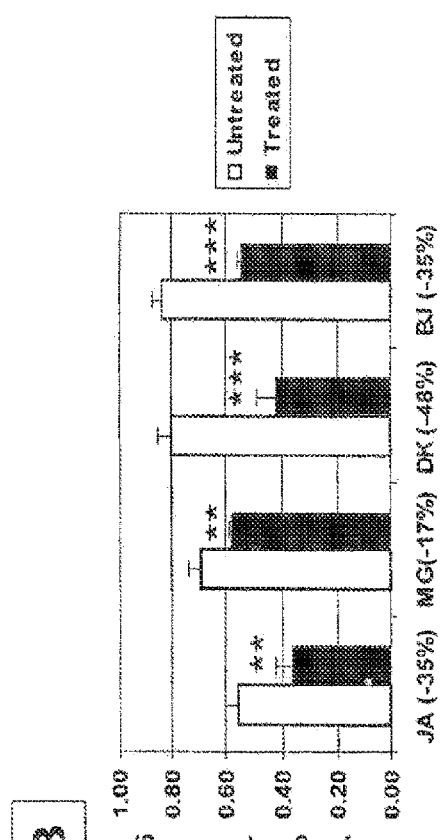
FIGS. 6A and 6B. rhGAA uptake and glycogen reduction in GSD-III muscle cells after 48-hour treatment (from Day 13 to Day 15) with 100 µg of rhGAA. Muscle cells from normal subject were treated from Day 7 to Day 10. (*, p value<0.05; , p<0.005; *, p<0.001).
Figure 6B:
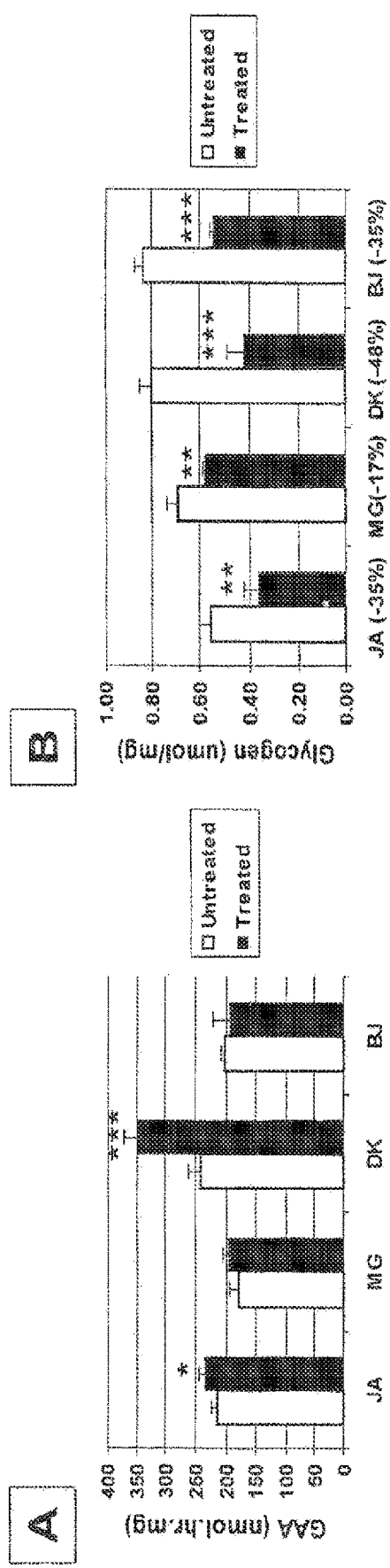

Differentiation of myoblasts into mature myotubes (myogenesis) was induced by incubation of the muscle cells in low-serum differentiation medium (low-glucose DMEM (GIBCO) containing 2% Hyclone H1 horse serum (Sigma), 0.5 mg/ml Fetuin, 0.5 mg/ml BSA, 0.025 mg/ml gentamycin and 0.125 µg/ml Amphotericin B (Clonetics). Glycogen was stored in fully differentiated GSD-III muscle cells when sufficient glucose was supplied in the medium (FIG. 4). Incomplete glycogenolysis was seen in GSD-III cells, but not in normal control cells after 48-hour glucose starvation (FIG. 5), indicating lack of debranching enzyme activity in the GSD-III patients. Fully differentiated GSD-III myotubes were treated for 48 hours by adding 100 µg of rhGAA (i.e., MYOZYME (Genzyme)) into the culture medium. GAA enzyme activity and glycogen content were analyzed biochemically and histologically in these cells. Treatment with rhGAA significantly reduced glycogen level by 48%, 35% and 17%, respectively, in the three GSD-IIIa patient muscle cells (FIG. 6). These data suggest the role of GAA in glycogen clearance in conditions where the primary defect results in cytoplasmic glycogen accumulation.

---

The invention claimed is:

1. A method of treating glycogen storage disease type VI, comprising administering to a human in need thereof a composition comprising acid α-glucosidase.

2. The method of claim 1, wherein the amount of the acid α-glucosidase administered is from about 1 mg to about 40 mg of acid α-glucosidase per kilogram of body weight.

3. The method of claim 1, wherein the acid α-glucosidase is a recombinant acid α-glucosidase, a precursor of recombinant acid α-glucosidase, or a combination thereof.

4. The method of claim 1, wherein the acid α-glucosidase is administered intravenously.

5. The method of claim 1, wherein the acid α-glucosidase is administered intrathecally.

6. The method of claim 1, further comprising administering an immunosuppressant, an immunotherapeutic agent, or a combination thereof, concurrently or sequentially.

7. The method of claim 1, wherein the acid α-glucosidase is administered daily.

8. The method of claim 1, wherein the acid α-glucosidase is administered weekly.

9. The method of claim 1, wherein the acid α-glucosidase is administered twice weekly.

10. The method of claim 1, wherein the acid α-glucosidase is administered monthly.

11. The method of claim 1, wherein the acid α-glucosidase is administered bi-monthly.

12. The method of claim 1, wherein the acid α-glucosidase is administered orally, intramuscularly, intraventricularly, or a combination thereof.

13. The method of claim 3, wherein the recombinant acid α-glucosidase or the precursor of recombinant acid α-glucosidase is produced in Chinese hamster ovary cells.

14. The method of claim 1, wherein the acid α-glucosidase is human.

\* \* \* \* \*